United States Patent [19]

Misra

[11] Patent Number: 5,182,410
[45] Date of Patent: Jan. 26, 1993

[54] ORGANO-ALUMINUM HYDROXIDE COMPOUNDS

[75] Inventor: Chanakya Misra, Pittsburgh, Pa.

[73] Assignee: Aluminum Company of America, Pittsburgh, Pa.

[21] Appl. No.: 627,748

[22] Filed: Dec. 14, 1990

[51] Int. Cl.$^5$ .............................................. C07F 5/06
[52] U.S. Cl. ............................... 556/187; 556/170; 556/182; 556/183
[58] Field of Search ................ 556/170, 182, 187, 183

[56] References Cited

U.S. PATENT DOCUMENTS

| | | | |
|---|---|---|---|
| 4,010,247 | 3/1977 | Wassermann et al. | 423/626 |
| 4,327,032 | 4/1982 | Lohse et al. | 260/448 |
| 4,447,364 | 5/1984 | Staal | 260/448 R |
| 4,559,220 | 12/1985 | Kullenberg et al. | 423/556 |
| 4,601,340 | 7/1986 | Fodor et al. | 166/294 |

Primary Examiner—Jose G. Dees
Assistant Examiner—Porfirio Nazario
Attorney, Agent, or Firm—Andrew Alexander

[57] ABSTRACT

Disclosed is a crystalline compound and a method for forming the compound having a chemical composition expressed, in terms of molar ratios, by the formula:

$$M.n[R(COOH)_x]$$

wherein M is aluminum hydroxide, n is the number of moles of organic material reacted with a mole of M, R is an organic functional group having carboxylic acid attached thereto, and x is equal to or greater than 2.

110 Claims, 14 Drawing Sheets

GIBBSITE

OXALIC ACID

MALEIC ACID

SUCCINIC ACID

GLUTARIC ACID

CITRIC ACID

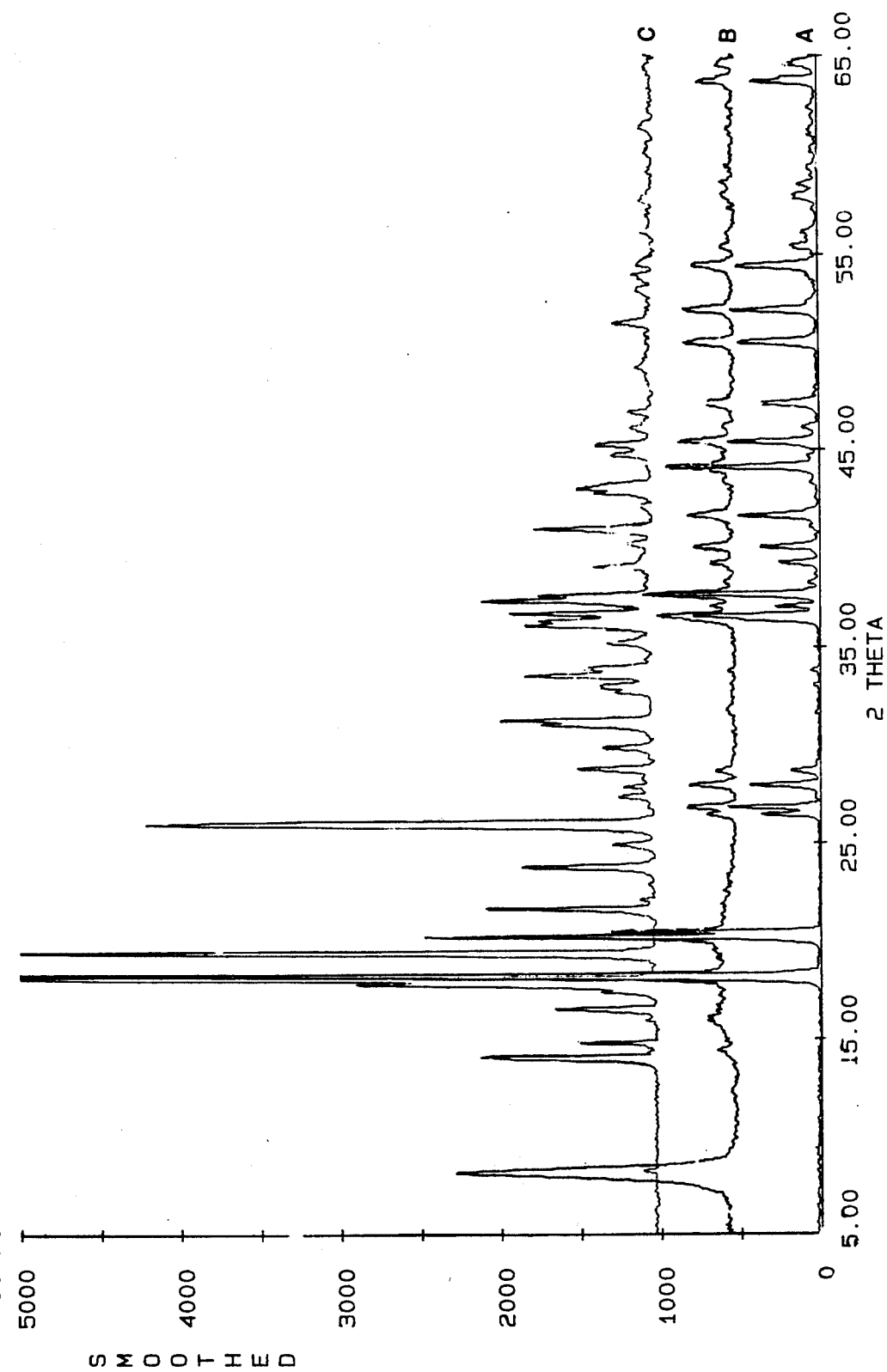

PIMELIC ACID

ITACONIC ACID

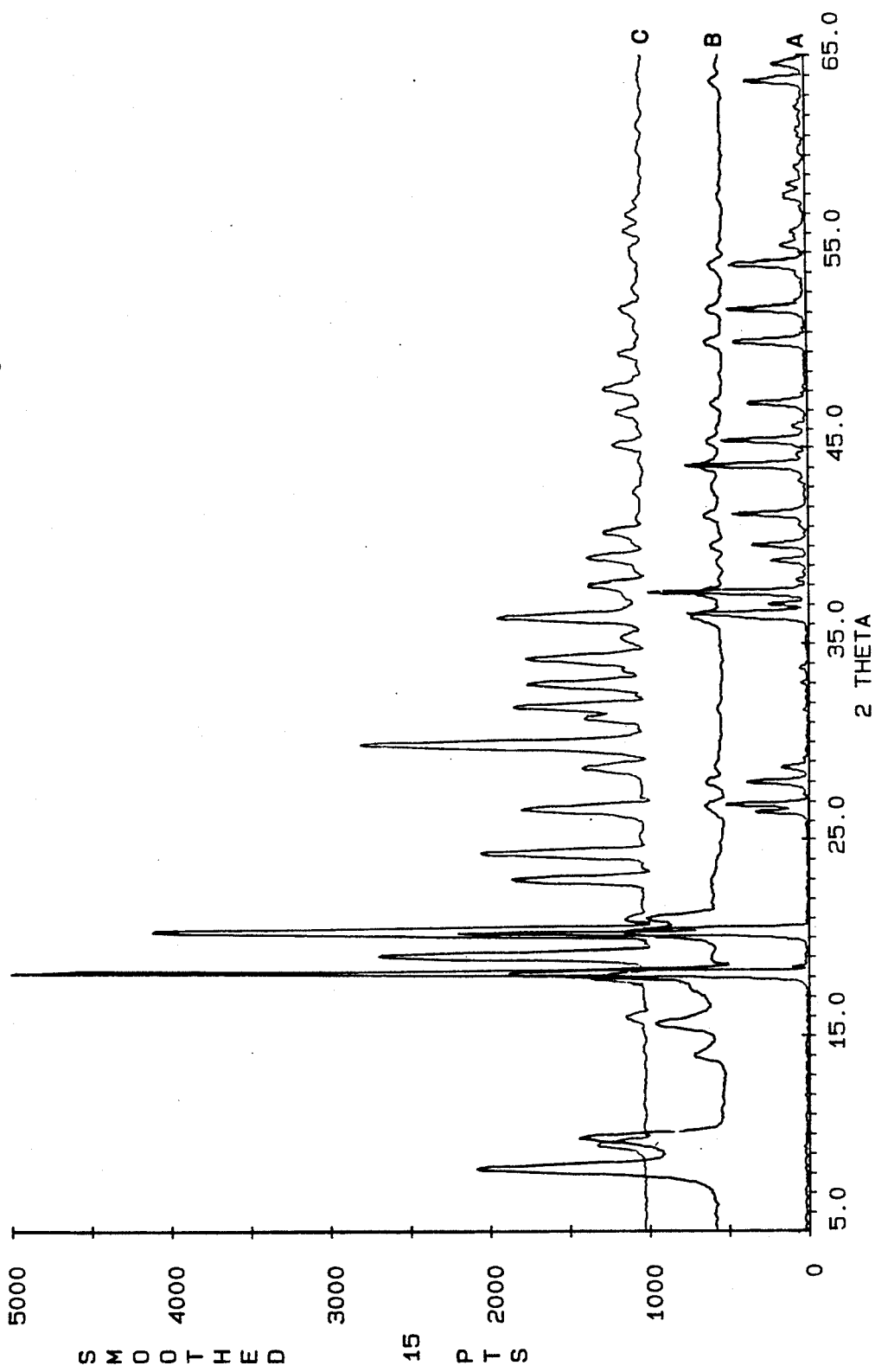

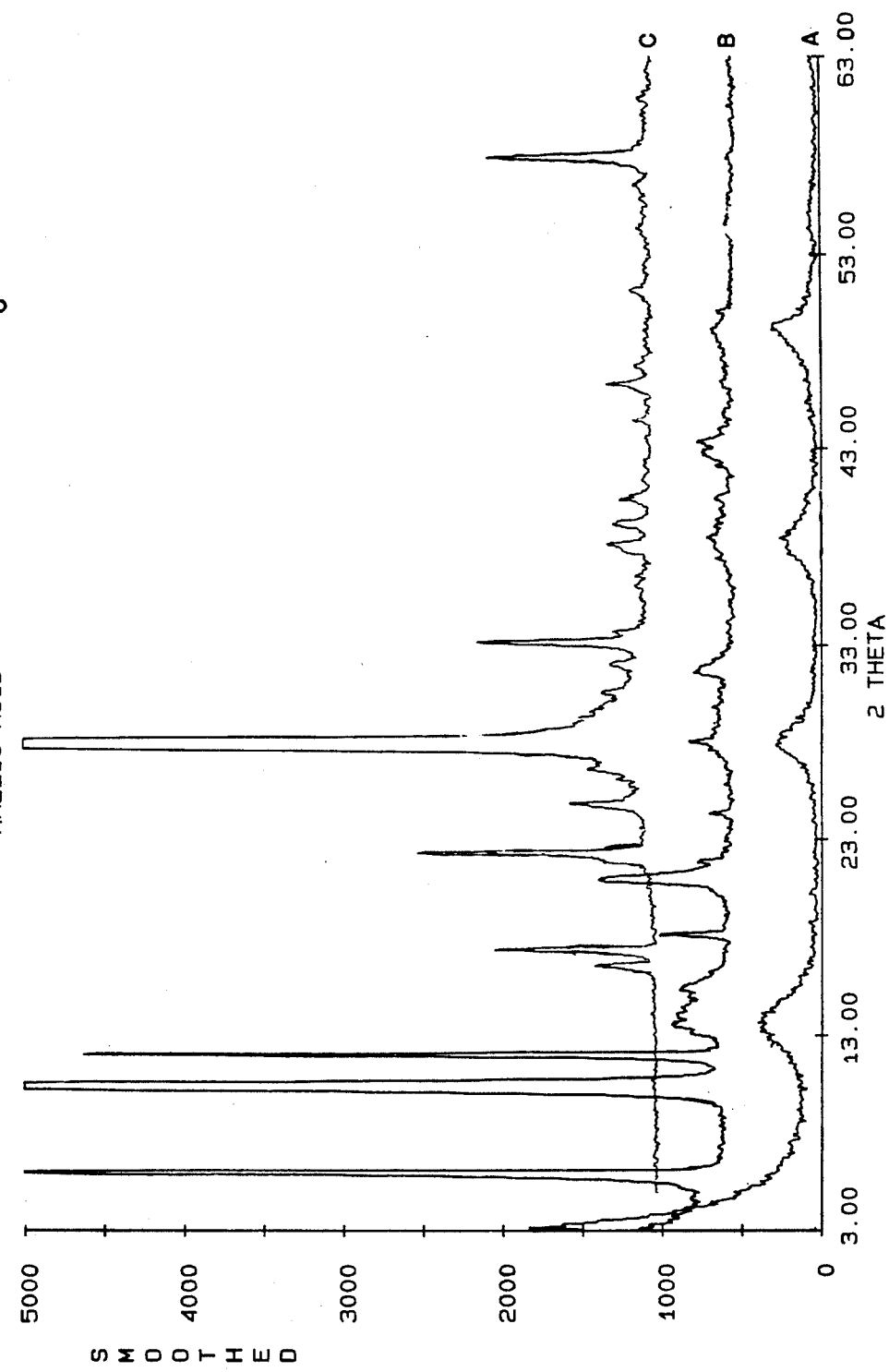

BOEHMITE/MALEIC ACID

ORGANO-ALUMINUM HYDROXIDE COMPOUNDS

INTRODUCTION

The present invention relates to aluminum hydroxide compounds, and more particularly, it relates to new crystalline compounds formed with aluminum hydroxide and acids and the method of making the compounds.

Because of the many uses to which aluminum hydroxide can be put, there is always great interest in modifying it to provide improved properties. For example, U.S. Pat. No. 4,559,220 discloses the production of polyaluminum hydroxide sulfate complexes where it has been found necessary in certain cases to stabilize these complexes with citric acid or some other α-hydroxycarboxylic acid to render the aqueous solutions of such complexes more stable in storage. Further, U.S. Pat. No. 4,010,247 discloses a method for making water-dispersible aluminum hydroxide where the aluminum hydroxide is treated with an inorganic or organic acid such as acetic acid.

U.S. Pat. No. 4,327,032 discloses aluminum monohydroxide salts of a carboxylic acid which are free from water of crystallization.

The present invention provides a method for intercalation of polycarboxylic acids into the crystal lattice of aluminum hydroxide or the combining of polycarboxylic acids with aluminum hydroxides to produce novel compounds thereof. In addition, the novel compounds may be further treated to produce novel alumina materials.

SUMMARY OF THE INVENTION

It is, therefore, an object of the present invention to provide a method for making novel compounds comprised of aluminum hydroxide and polycarboxylic acids.

It is a further object of the present invention to provide a method for making novel compounds comprised of aluminum hydroxide and dicarboxylic acids.

It is yet a further object to provide a method of making novel compounds of aluminum hydroxide, e.g., alumina trihydrate ($Al_2O_3.3H_2O$) and dicarboxylic acids.

Yet it is another object of this invention to provide novel compounds of aluminum hydroxide and polycarboxylic acids.

Further, it is an object of the present invention to provide a method for producing high surface area alumina having controlled pore size.

It is another object of the present invention to provide a method for producing new products of aluminum hydroxide and polycarboxylic acids having a morphology different from the starting aluminum hydroxide.

In accordance with these objects, there is provided a crystalline compound and a method for forming the compound having a chemical composition expressed, in terms of molar ratios, by the formula:

M.n[R(COOH)$_x$]

wherein M is aluminum hydroxide, n is the number of moles of organic material capable of reacting with a mole of M, R is an organic functional group and x is equal to or greater than 2.

BRIEF DESCRIPTION OF THE DRAWINGS

FIG. 11 shows X-ray diffraction lines characteristic of a new compound resulting from gibbsite and citric acid.

FIG. 15 shows X-ray diffraction lines characteristic of a new compound resulting from gibbsite and itaconic acid.

FIG. 17 shows X-ray diffraction lines characteristic of a new compound resulting from gibbsite and maleic acid.

DETAILED DESCRIPTION OF THE PREFERRED EMBODIMENT

Figure 1:
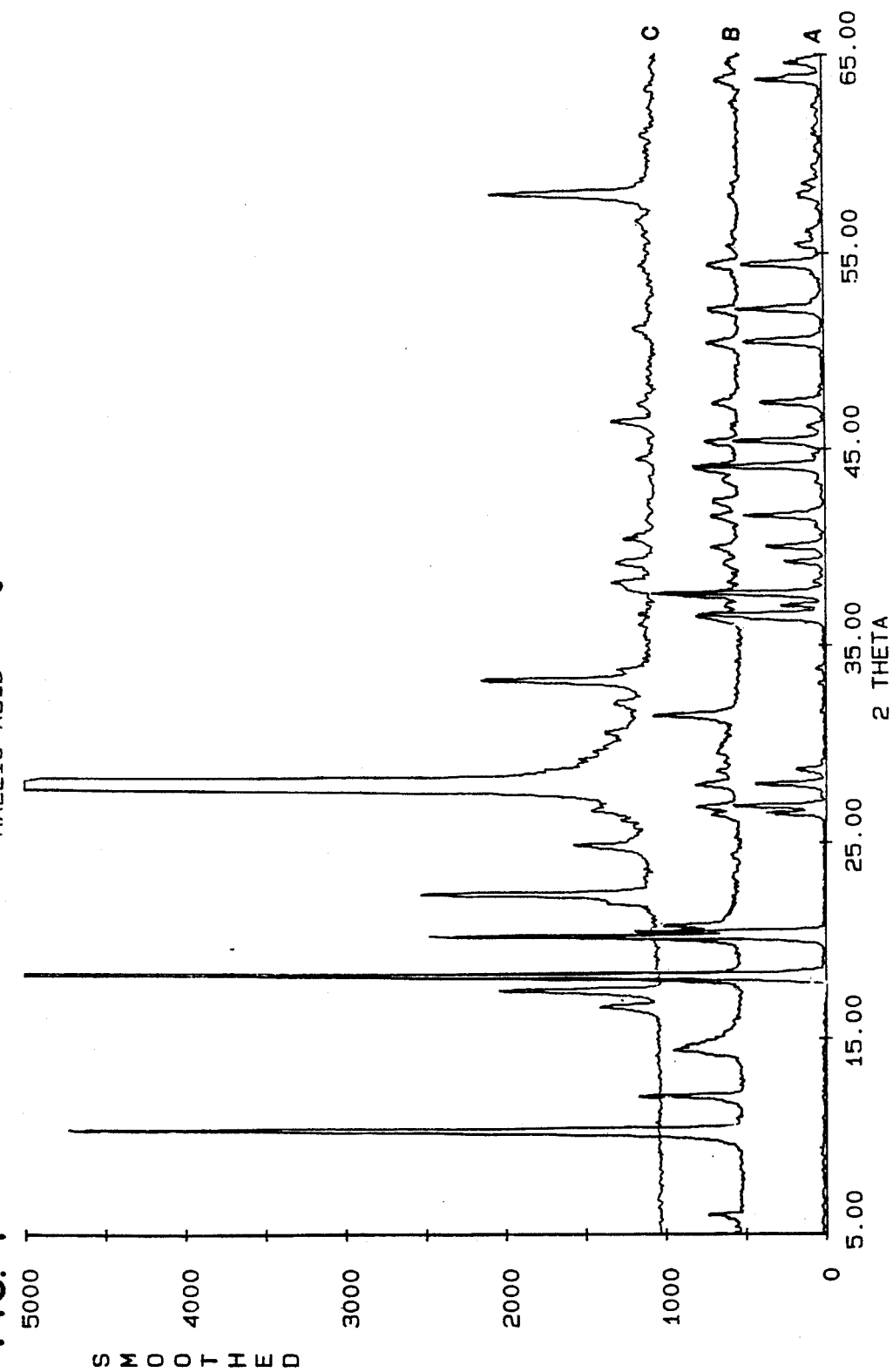
FIG. 1 shows X-ray diffraction lines characteristic of a new compound resulting from gibbsite and oxalic acids.

The subject invention provides a family of novel, water insoluble compounds comprised of aluminum hydroxide, e.g., gibbsite, bayerite, boehmite, nordstrandite, etc., and polycarboxylic acids. The novel compounds are anhydrous as formed. By anhydrous compounds is meant that the compounds as formed do not have water of crystallization. Thus, there is no need to remove water of crystallization by heating, refluxing, azeotropic distillation or drying under vacuum, etc. The use of aluminum hydroxide herein is meant to include $Al_2O_3.3H_2O$ and $Al(OH)_3$ which are sometimes referred to as alumina trihydrate, hydrated alumina, hydrated aluminum oxide or aluminum trihydroxide. Further, aluminum hydroxide as used herein is intended to define a broad spectrum of hydroxides ranging from those which may contain few hydroxides, e.g., activated or partially calcined forms of aluminum oxide (alumina) to more hydrated forms which may comprise mainly hydroxide, e.g., $Al(OH)_n$ wherein n equals 1 to 3. It has been found, however, that the metal hydroxide form, rather than the metal oxide form, provides a more desirable product with the carboxyl-containing group on the organic molecule with which it is reacted. However, for certain applications, dehydrated or activated forms of the aluminum hydroxide may be preferred due to the higher surface area of such particles.

While the invention is primarily directed to the use of aluminum hydroxide particles as materials for reaction with the carboxyl-containing organic molecules to form the new material, it is within the purview of this invention that other metals, e.g., magnesium, gallium, zinc, could be used in substitution for aluminum. Other metal oxide/hydroxides which may be considered include In, Fe, Sc, Mn and Y. Further, it is contemplated within the purview of the invention that other metal compounds could be used for the aluminum hydroxides such as metal nitrates, halogenides, phosphate, sulfates, carbonates, apatites, hydrotalcites, zeolites, kaolin and clays as well as combinations of any of such materials with the aluminum hydroxide materials.

With respect to the aluminum hydroxides used in the present invention, it is preferred that they are provided in particulate form for certain applications. Particle sizes can range from as low as 50 Å to provide large external surfaces and up to 250 $\mu$m to produce large particle size products. Typically, the particle size is 0.1 to 100 microns. It will be appreciated that uses, for example, flocculation, flame retardance in polymers, heterogeneous catalysts and adsorbents, can require different particle sizes. However, normally the particle size is greater than 0.1 micron. Typical particle size distributions, when the particles comprise aluminum hydroxide, are 0.1-1, 3-6, 7-12, 10-18, 18-32, 32-63 and 50-200 microns.

With respect to particle morphology of the aluminum hydroxides used in the invention, both crystalline and gel type, including pseudoboehmite aluminum hydroxides, can be used. With respect to purity, the level of impurity should be minimized depending on the end use. For adsorbents, for example, the metal hydroxide should have a purity level of over 80%, preferably 95% or greater. Surface area of the particle is preferred to be high with typical surface areas, for example, being in the range of 0.10 to 600 $m^2/g$.

To produce the novel material comprising the aluminum hydroxide reacted with one or more types of di- or tri- carboxyl-containing organic molecules, the reaction is carried out in an aqueous containing medium, e.g., water and an organic solvent. However, prior to the reaction, the carboxylic acid containing organic molecule may be first dissolved in a solvent or medium such as water or an alcohol or a water-alcohol combination. Alcohols which may be used include methanol, ethanol, propanol and butanol or the like. Butanol and higher carbon, e.g., 5 or 6 carbon, alcohols may be used at higher than room temperature. For example, when oxalic acid is being dissolved, a solvent may contain only water. Carboxylic acid concentrations in the solvent or medium can range from 0.01 to 3 molar. Preferably, 0.05 to 2.0 moles of acid is used for each mole of aluminum hydroxide. The amount of acid in the aqueous medium can vary depending on the carboxylic acid being used. For example, 0.1 molar may be used for oxalic acid, and 1.0 molar may be used for succinic or glutaric acids. Further, the solvent can be a medium other than water or alcohol, depending on the organic group to which the carboxylic acid is attached. Thus, it will be appreciated that any organic solvent is intended to be encompassed within the purview of the invention, depending largely on the organic compound being attached to the aluminum hydroxide particle.

The polycarboxylic acid useful in the present invention contains at least two carboxyl groups. Typical of these are oxalic acid $HO_2CCO_2H$; malonic acid $HO_2CCH_2CO_2H$; maleic acid cis-$HO_2CCH=CHCO_2H$; succinic acid $HO_2CCH_2CH_2CO_2H$; glutaric acid $HO_2CCH_2CH_2CH_2CO_2H$; alipic acid $HO_2CCH_2CH_2CH_2CH_2CO_2H$; fumaric acid trans-$HO_2CCH=CHCO_2H$; tartaric acid $HO_2CCH(OH)CH(OH)CO_2H$; citric acid $HOC(CH_2CO_2H)_2CO_2H$; and itaconic acid $CH_2=CH(CO_2H)CH_2CO_2H$. Different acids can result in novel crystal shapes and structures of aluminum hydroxide-carboxylic acid compounds. Further, recovery of aluminum oxide from such a compound permits the control of the surface area and pore size, for example, of the aluminum oxide if it is desired to produce aluminum oxide from the novel compound.

Aluminum hydroxide, as noted earlier, is added in an amount which permits a controlled molar ratio of aluminum hydroxide to carboxylic acid, e.g., 0.1 to 2.0 moles of carboxylic acid per mole of aluminum hydroxide. After addition of aluminum hydroxide to the solvent to provide a mixture thereof, the temperature may be raised above room temperature, e.g., 150° C., to permit reaction between aluminum hydroxide and carboxylic acid to take place. Thus, the temperature can range from 25° C. to 300° C. or 400° C., with temperatures of 100 to 250° C. having been found to be quite suitable for dicarboxylic acids. The time at temperature should be sufficient for the reaction to take place and may be as short as a few minutes or extend for several hours or longer with typical times being about 1 to 10 hours. For example, 2 to 4 hours have been found to be adequate digesting for a dicarboxylic acid to react with aluminum hydroxide such as Bayer alumina hydrate. Further, these times and temperatures are also dependent on the concentration of the carboxylic acids.

For purposes of heating a mixture of the aluminum hydrate and carboxylic acid solution, it has been found that a closed vessel is beneficial. The closed vessel permits pressure to build autogenously.

The reaction is carried out at higher than atmospheric pressure, preferably from about 2 psi to 250 psi above atmosphere and typically about 5 to 200 psi above atmospheric pressure. The closed vessel is beneficial for controlling solvent loss.

After the aluminum hydroxide and polycarboxylic acid have been digested or reacted, the new product can be separated from the solvent media by filtering, for example. Thereafter, it may be washed and dried at temperatures below about 300° C.

The formula for the polycarboxylic acid useful in the practice of the invention may be written as $R(COOH)_x$ where x is equal to or greater than 2 and R may be comprised of 0-30, preferably 0-15, carbon-containing molecules such as an alkyl group. Other examples of groups which may comprise R include long and short chain aliphatic hydrocarbons, aromatic hydrocarbons, carboxylic acids, aldehydes, ketones, amines, amides, thioamides, imides, lactams, anilines, pyridines, piperidines, anhydrides, carbohydrates, thiocyanates, esters, lactones, ethers, alkenes, alkynes, alcohols, nitriles, oximes, organosilicones, sulfur-containing organic compounds, ureas, thioureas and combinations of these groups.

The polycarboxyl-containing organic molecules such as above may also include inorganic groups substituted thereon such as halogens, nitrates, phosphates, phosphinates, phosphinites, phosphonates, quaternary ammonium salts, and the like. It is within the scope of the present invention to provide, on a free end of the molecule, one or more functional groups. A functional group may be defined as the group on the molecule which enables the reactive material (comprising the polycarboxyl-containing organic material reacted with the aluminum hydroxide) to react with, attract, couple to, bond with, etc. other atoms, ions and/or molecules. Intermediate groups may be defined as the groups on the molecule which permit substitution or addition of groups or compounds to the R group after the novel product has been formed. Examples of intermediate groups include I, Cl, Br, CN, etc. The intermediate group permits the addition of groups or radicals which would not be compatible with or be destroyed during the reaction with the aluminum hydroxide. Thus, this permits the addition of functional groups to the R group after the reaction. By attaching specific functional groups, either organic or inorganic, to the R group of the carboxylic acids, a wide variety of products can be formed.

The functional groups attached to or contained within the R group can be selected from cation exchange functional groups and anion exchange functional groups such as $-HSO_3$, $-N(CH_3)_3Cl$, $-COONa$, $-NH_2$ and $-CN$, for example.

While the inventor does not wish to be bound by any particular theory of reaction, it is believed that when an aluminum hydroxide particle, for example, gibbsite, is brought into contact with a carboxylic acid, a reaction or intercalation, or a combination thereof, of the acid on the aluminum hydroxide takes place in which the aluminum and carbon atoms in the respective molecules are apparently bonded together through an oxygen atom.

It is believed that in one aspect of the reaction, intercalation of the organic acid in the hydroxide layers of the aluminum hydroxide is obtained, that is, not just surface hydroxides react. There is strong evidence that a novel compound is formed as a result of this reaction. This is shown by the X-ray diffraction pattern obtained for the compound. That is, even though the pattern of the new compound has lines corresponding to that of the Al(OH)$_3$, additional new X-ray diffraction lines characteristic of the new compound are observed or are present, as will be seen in FIG. 1, for example. This, it is believed, evidences both the old structure of the Al(OH)$_3$ and the new structure of the novel compound. The new compound may be defined by the formula, expressed in terms of molar ratios:

$M \cdot n[R(COOH)_x]$ where M is a metal hydroxide, preferably aluminum hydroxide. As noted earlier, other metals or other metal compounds such as enumerated earlier may be substituted for aluminum. Also, n is a number in the range of 0.01 to 3, preferably 0.05 to 2.0 and is the number of moles of organic material attached to a mole of M. R is an organic functional group and COOH is a carboxyl group, and x is equal to or greater than 2 and can be 3 or 4, for example.

Thus, it can be seen that hydroxyl groups in gibbsite, as well as those on the surface, can be reacted with the carboxylic acid groups. It is believed that during the reaction, there is a dissolution of the gibbsite followed by a reprecipitation of the new compound. Consideration is also given to the fact that an intercalation type reaction occurs between the carboxylic acid and the hydroxyl groups located between the layers of aluminum in the gibbsite.

Figure 2:
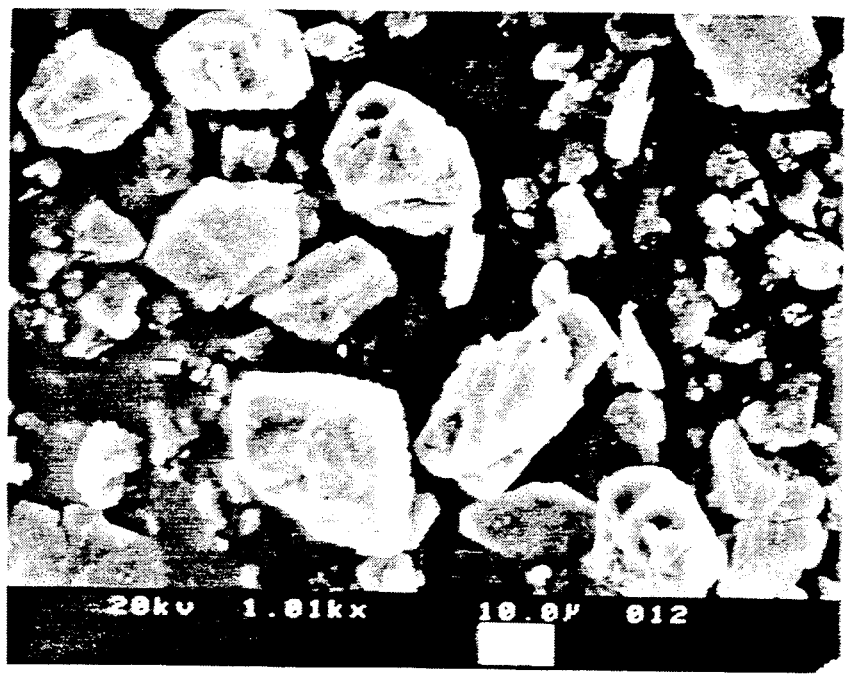
FIG. 2 is a micrograph showing particles of gibbsite.
Figure 3:
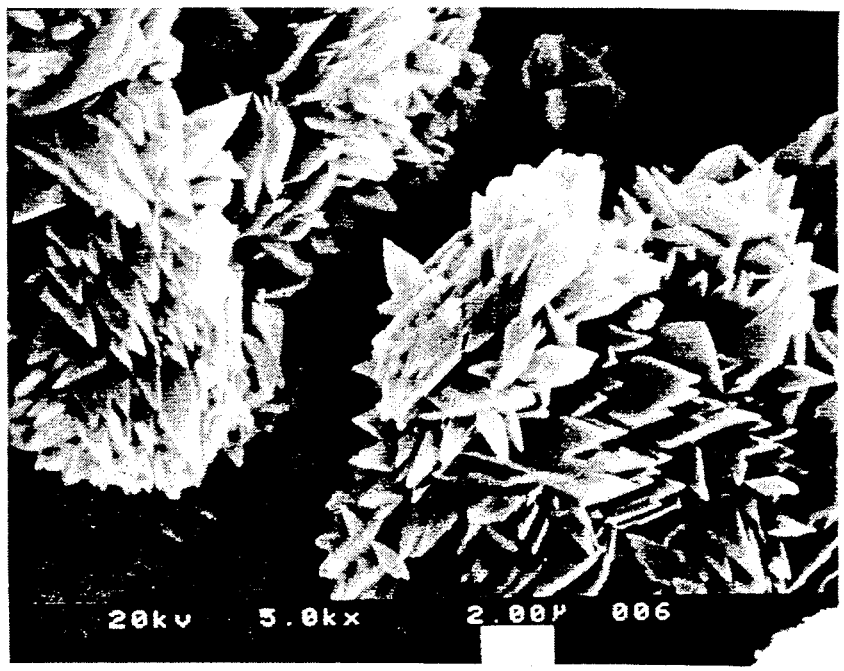
FIG. 3 is a micrograph showing expanded particles of the new compound resulting from gibbsite and oxalic acid.

As presently understood, the carboxyl groups not only bond to surface hydroxide but also permeates into the layers of hydroxyl units joining the layers of aluminum atoms. From an examination of FIG. 2, it will be seen that aluminum hydroxide particles (original gibbsite) are shown as solids. However, these particles, after reaction, are shown as greatly expanded particles which only generally depict the outline of the particles formed from platelets, needles, joined at the center (see FIG. 3). The particles of the new compound may have the general outline of the original particle but are composed of differently interwoven threads, strips, plates and rods.

X-RAY DIFFRACTION

The X-ray diffraction patterns show the presence of the original compound, e.g., gibbsite, as well as new lines specific to the acid used (see FIG. 1). However, these new lines do not correspond to the carboxylic acid used or to the aluminum salt of the acid where such a salt is known to exist. For example, the X-ray diffraction pattern of aluminum oxalate is reported in the Powder Diffraction File (JCPDS) published by International Centre for Diffraction Data, Swarthmore, Pa. 19081. This pattern is seen to be quite different from the pattern obtained for the aluminum hydroxide-oxalic acid compound described in Example 1.

ACTIVATION

The new compounds which contain a polycarboxylic acid can be heated to produce activated alumina. That is, upon heating, the polycarboxylic acid will decompose leaving activated alumina. Chi-Al$_2$O$_3$ has been obtained in many cases upon heating the product resulting from reaction of gibbsite with dicarboxylic acids. Surface area after heating to 300° C. can be greater than 500 m$^2$/g for maleic acid reacted gibbsite. However, for higher molecular weight carboxylic acids, e.g., succinic acid, the surface area can be lower, e.g., 200 m$^2$/g.

PORE SIZE

Activated alumina resulting from calcination of the new compound results in a larger pore size. For example, pore size as measured by Hg and N$_2$ porosinetry is in the range of 20 to 200 Å, typically 80 to 120 Å in diameter. This may be compared to less than 30 Å for gibbsite, for example.

Na$_2$O

The new compounds have as a benefit purification of the original aluminum hydroxide with respect to Na$_2$O content. For example, the Na$_2$O content of gibbsite obtained from the Bayer process is dramatically lowered from 0.25 wt. % to 0.01 wt. %.

THERMAL ANALYSIS

Figure 4:
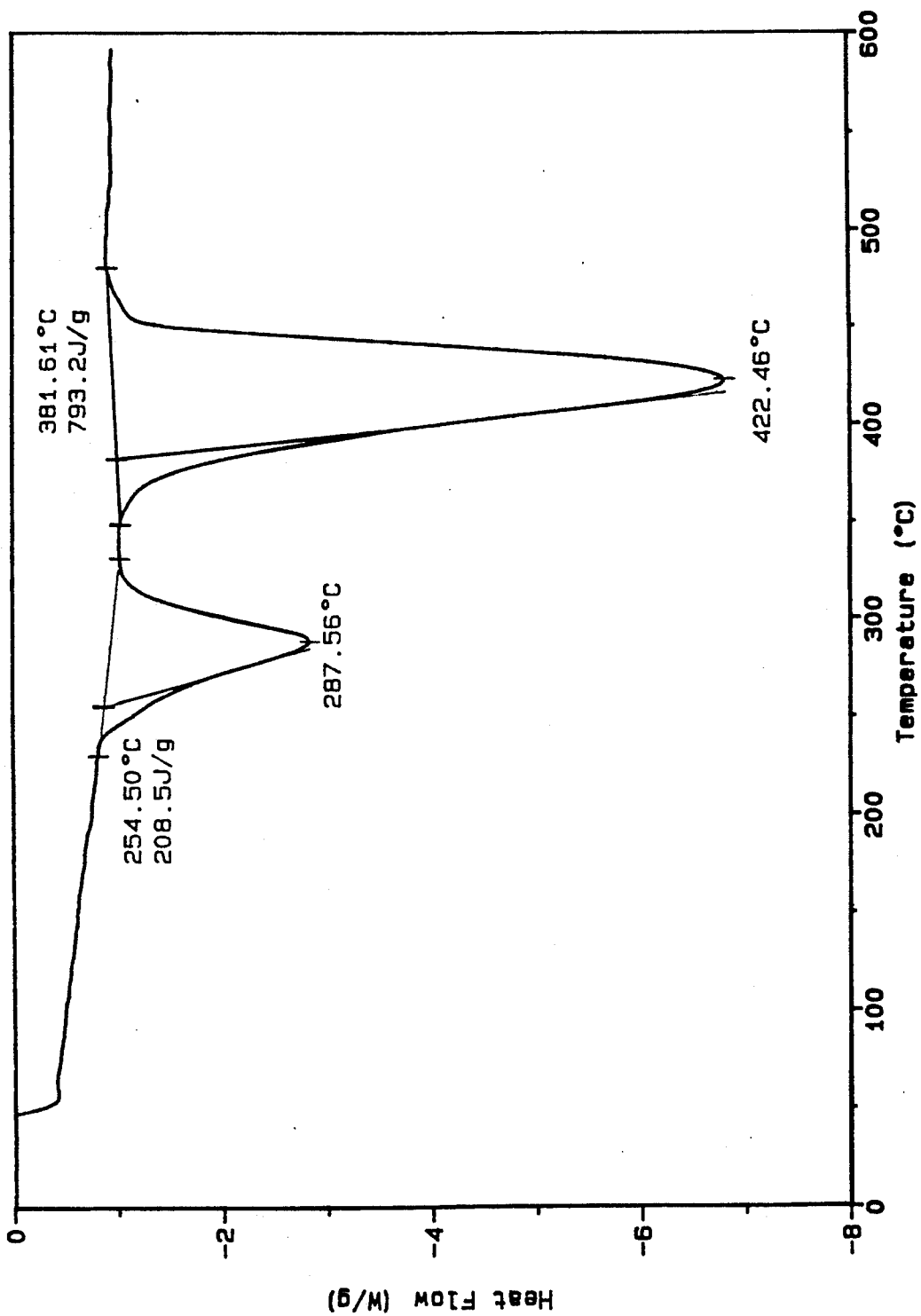
FIG. 4 shows an endotherm for the gibbsite, oxalic acid product.

FIG. 4 shows a large endotherm for the oxalic acid product. The total endothermic heat absorption is 10% higher than for gibbsite and occurs about 50°-100° C. higher than for gibbsite. In the case of the other acids, decomposition in air results in exothermic heat release at about 500° C. due to the combination of the organic fraction. Analysis in N$_2$ shows an endotherm at about 100° C. higher than for gibbsite. Weight loss on heating to >1000° C. is in the range of 40-65 wt. % (compared to 35 wt. % for gibbsite) depending on the acid used. A fine particle size α-Al$_2$O$_3$ is obtained above 1000° C.

Applications of the new group of aluminum hydroxide-carboxylic acid compounds include: (1) high surface area active alumina for use as desiccants, adsorbents, catalysts and catalyst supports which are prepared by thermal decomposition of the compounds in the 200°-1000° C. temperature range; (2) controlled pore size activated alumina with pore sizes in the range of 20 to 200 Å suitable for use as adsorbents, catalysts and catalyst supports; (3) fire retardant additives to plastics where hydroxide-oxalic acid compound has been found to reduce fire propagation in polypropylene when added at 60 w/w load level; (4) fillers having functional groups which are capable of interacting with polymers, thus improving their strength properties; (5) alumina-carbon composite products prepared by controlled pyrolytic decomposition of the aluminum hydroxide-carboxylic acid compounds which have adsorption properties of both alumina and carbon; and (6) low soda, fine particle size α-Al$_2$O$_3$ for ceramic applications where decomposition above 1000° C. produces very low soda content (<0.02% Na$_2$O) fine crystallite size (<0.2 μm size) α-Al$_2$O$_3$ suitable for the preparation of high quality abrasive alumina powder and for alumina ceramics.

EXAMPLE 1

25 grams (20 μm particle size) Bayer process crystalline gibbsite was added to a solution of 40 grams of oxalic acid in 400 ml of water in a closed vessel which was constantly stirred. The vessel was heated to 165° C. for 4 hours and thereafter cooled to room temperature before being opened. The resulting product was filtered and washed with hot deionized water and dried at about 105° C. overnight. The new compound was analyzed by X-ray diffraction (XRD), NMR, IR and by SEM. FIG. 1 shows the XRD pattern of this new compound and is compared with the XRD of the starting gibbsite and oxalic acid. The XRD of the new compound shows new lines which characterize this compound. These lines are in addition to the XRD lines of the original gibbsite. However, it will be appreciated that the oxalic acid XRD lines are not present in the compound. The same behavior is confirmed by NMR and IR results. The SEM picture shows the morphology of the new compound formed (see FIG. 3). This may be compared with the SEM picture of the starting gibbsite. Chemical analysis of the new compound shows that 0.405 moles of oxalic acid had reacted with each mole of gibbsite. The XRD of the new compound and the crystal morphology show that a new compound has been formed under the above reaction conditions.

EXAMPLE 2

Figure 5:
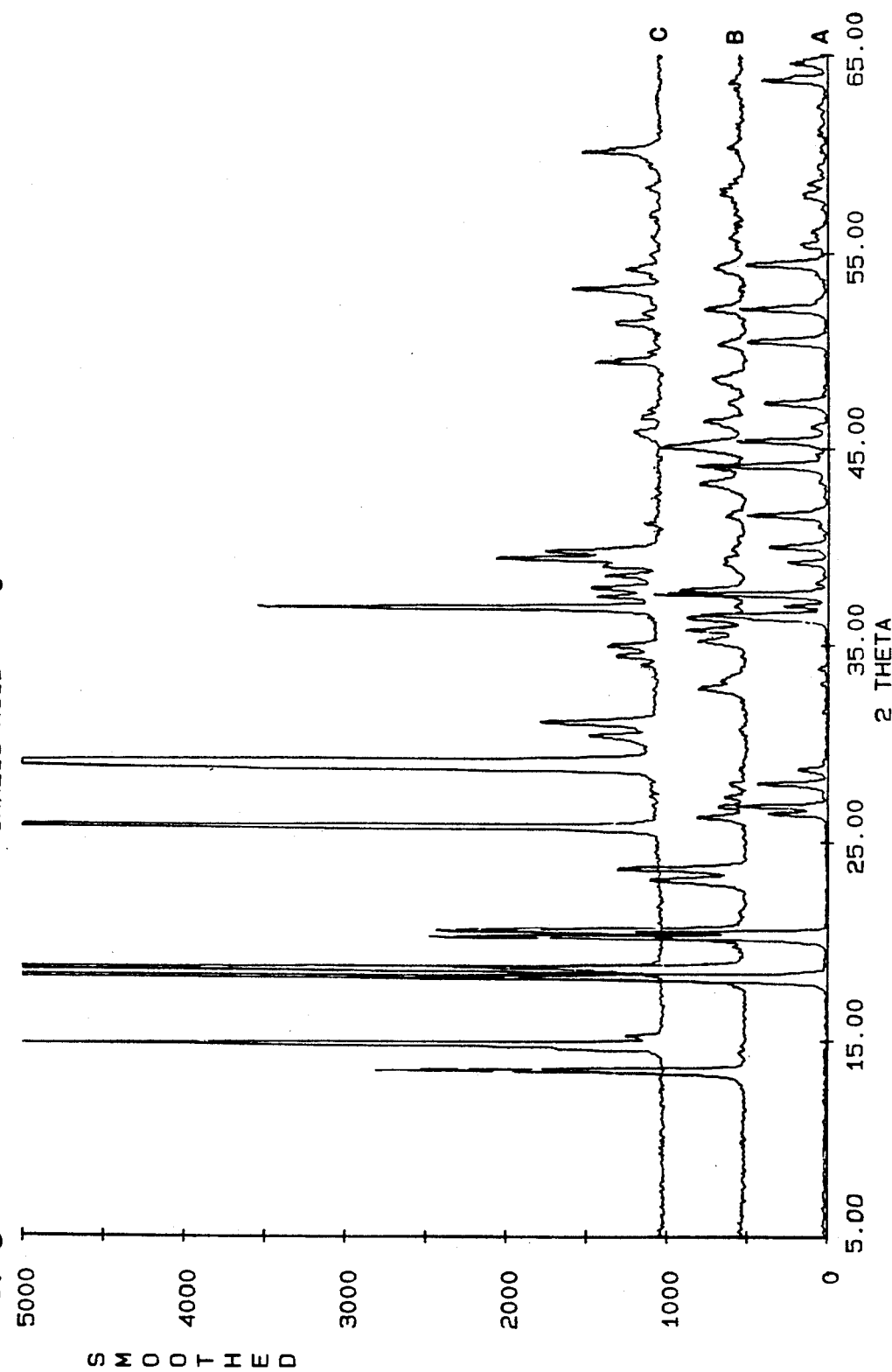
FIG. 5 shows X-ray diffraction lines characteristic of a new compound resulting from gibbsite and maleic acid.
Figure 6:
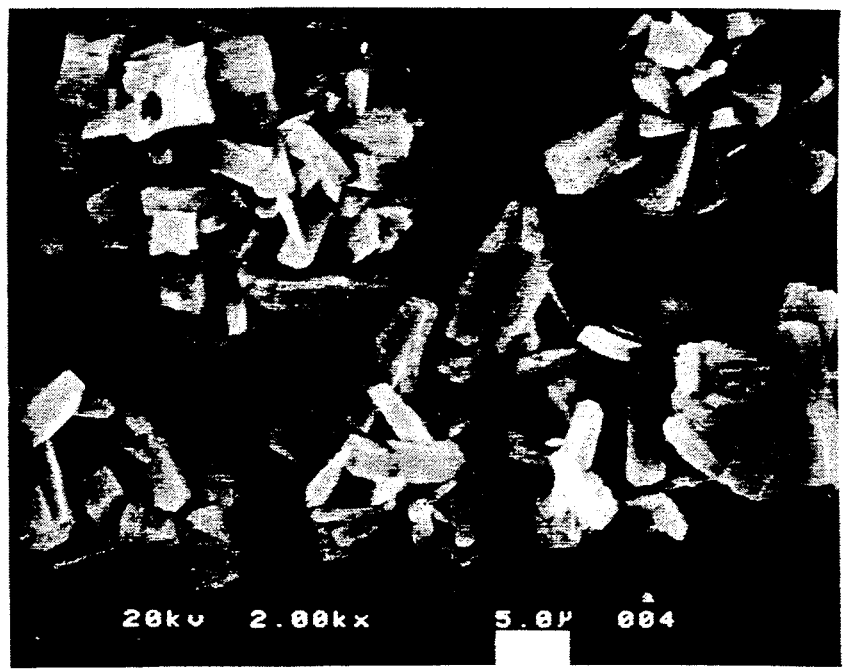
FIG. 6 is a micrograph showing the particle resulting from gibbsite and maleic acid.

This example was the same as Example 1 except maleic acid was used and the reaction temperature was 185° C. The new compound prepared was also studied using the same techniques as in Example 1. FIG. 5 is the new XRD pattern of the compound compared with the starting materials. Again, as in Example 1, new lines characteristic of this compound are seen. The chemical analysis of the new compound shows 0.283 moles of maleic acid had reacted with 1 mole of gibbsite. SEM is shown in FIG. 6. It will be noted that the morphology of this new compound is different from the starting aluminum hydroxide and the new product from Example 1.

EXAMPLE 3

Figure 8:
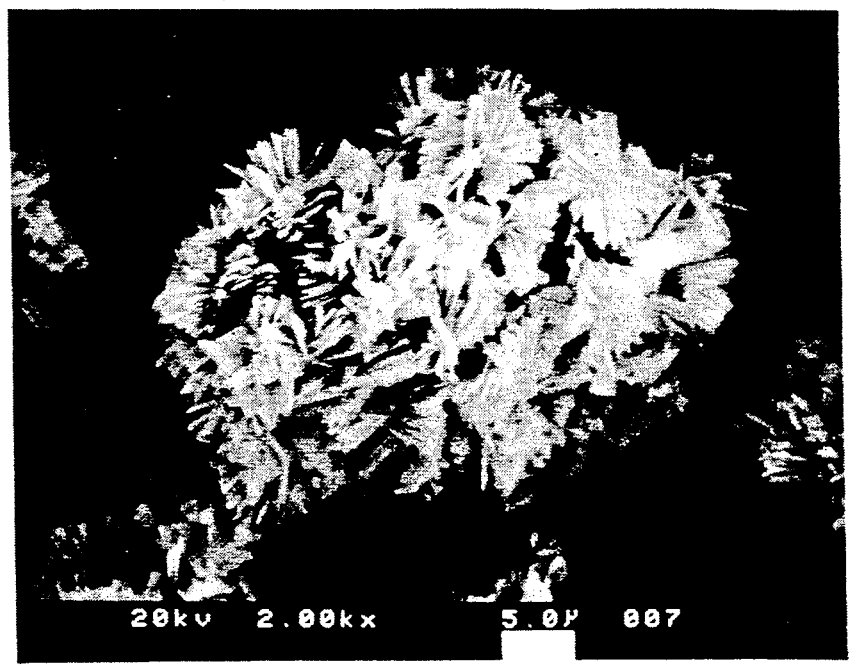
FIG. 8 is a micrograph showing the product resulting from gibbsite and succinic acid.
Figure 7:
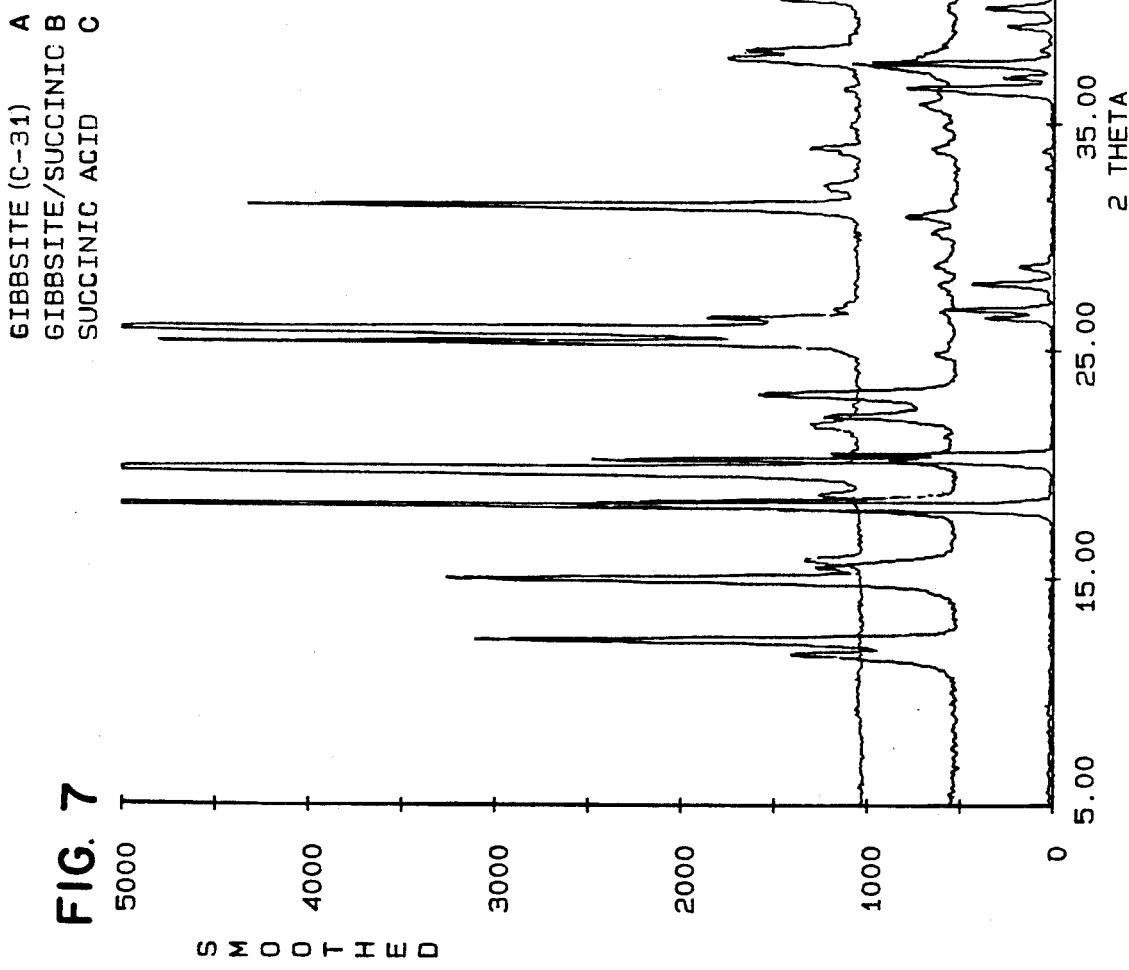
FIG. 7 shows X-ray diffraction lines characteristic of a new compound resulting from gibbsite and succinic acid.

This example is the same as Example 1 except succinic acid was used and the reaction temperature was 185° C. The new compound was analyzed using the technique in Example 1. FIG. 7 is an XRD pattern of the compound. Again, as in Example 1, new lines characteristic of this compound can be seen. The chemical analysis of the new compound shows that 0.75 moles of succinic acid reacted with each mole of gibbsite. The SEM is shown in FIG. 8. It will be noted that the morphology is different from the starting aluminum hydroxide and the compounds of Examples 1 and 2.

EXAMPLE 4

Figure 9:
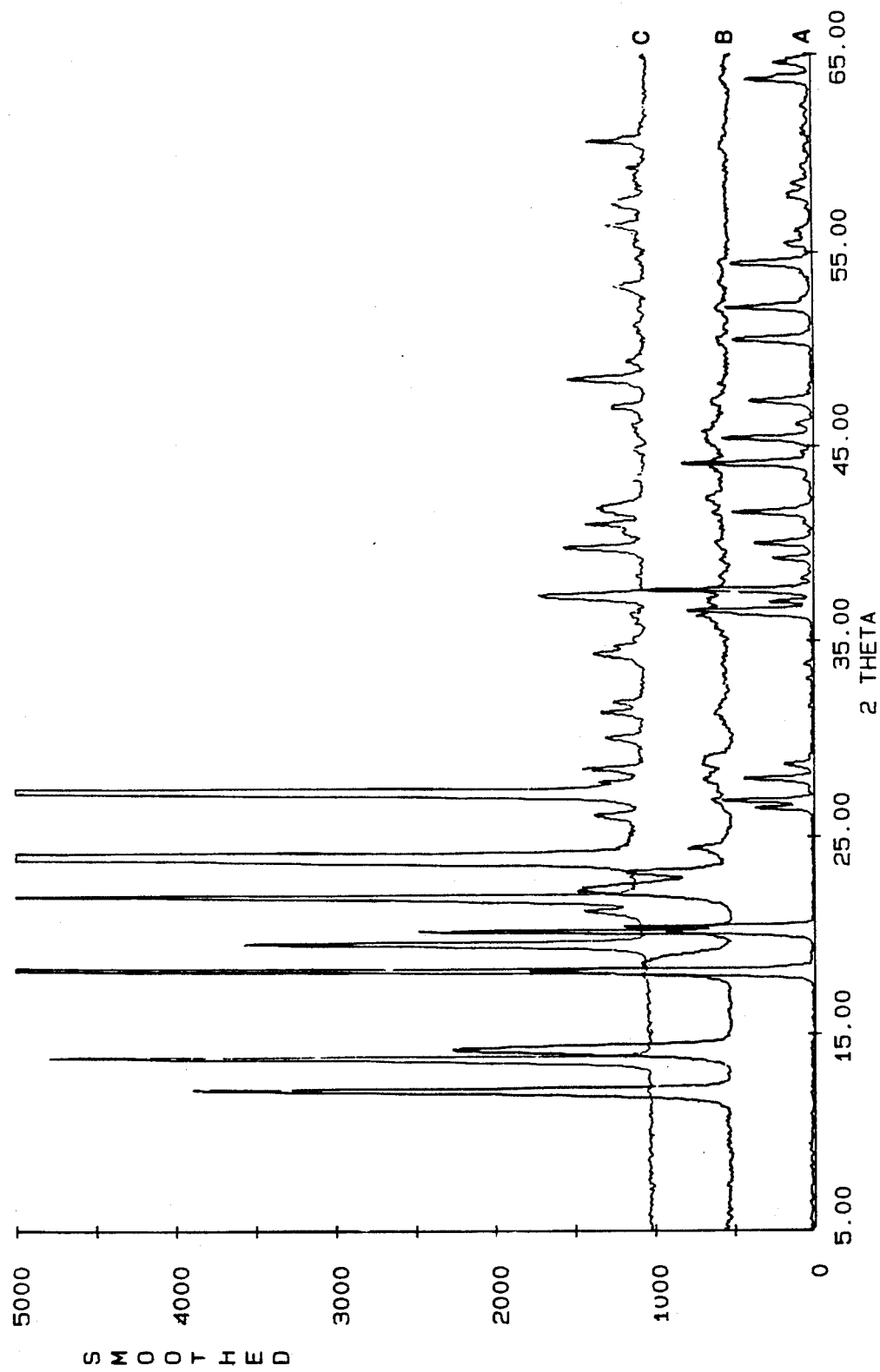
FIG. 9 shows X-ray diffraction lines characteristic of a new compound resulting from gibbsite and glutaric acid.
Figure 10:
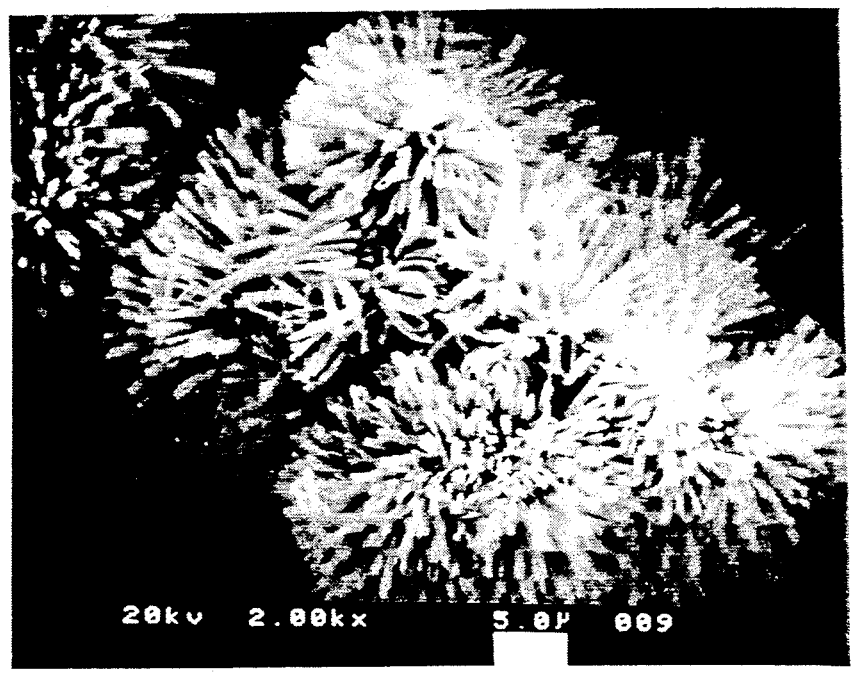
FIG. 10 is a micrograph showing the product resulting from glutaric acid.

This Example is the same as Example 3 except 50 grams of glutaric acid were used. The techniques that were used for analyzing the new product were the same as in Example 1. FIG. 9 is the new XRD of the compound compared to the starting materials. As in the prior examples, new lines characteristic of this compound are seen. The chemical analysis of the new compound shows 0.74 moles of glutaric acid had reacted with one mole of gibbsite. The SEM is shown in FIG. 10. Again, it will be noted that the morphology of this compound is different from the starting aluminum hydroxide and the other new products.

EXAMPLE 5

Figure 12:
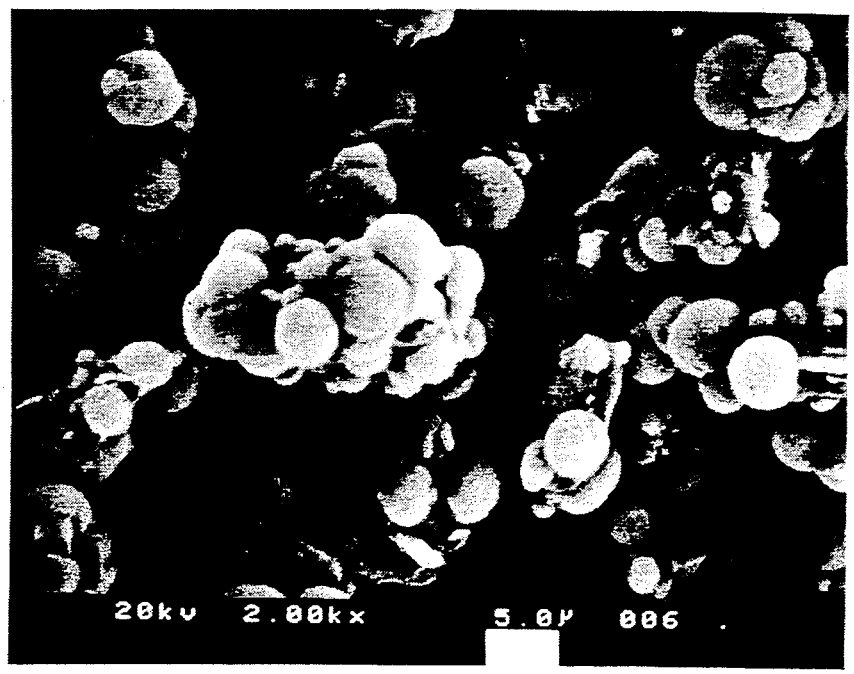
FIG. 12 is a micrograph showing the product resulting from gibbsite and citric acid.

This example was prepared and analyzed the same as Example 4 except citric acid was used. FIG. 11 shows the XRD pattern of the new compound compared to the starting materials, chemical analysis of the new compound, shows that 0.182 moles of citric acid had reacted with 1 mole of gibbsite. The SEM is shown in FIG. 12.

EXAMPLE 6

Figure 13:
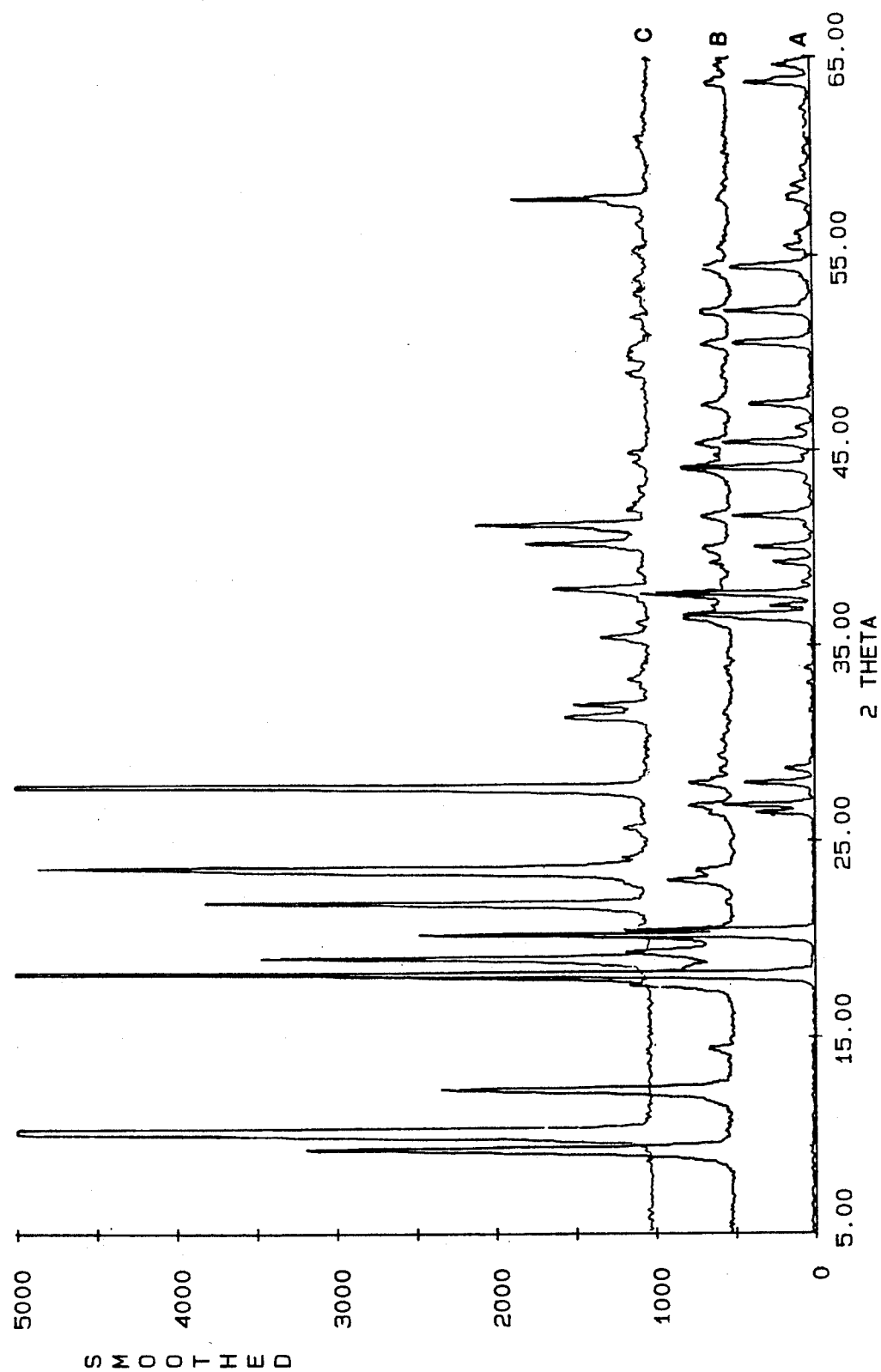
FIG. 13 shows X-ray diffraction lines characteristic of a new compound resulting from gibbsite and pimelic acid.
Figure 14:
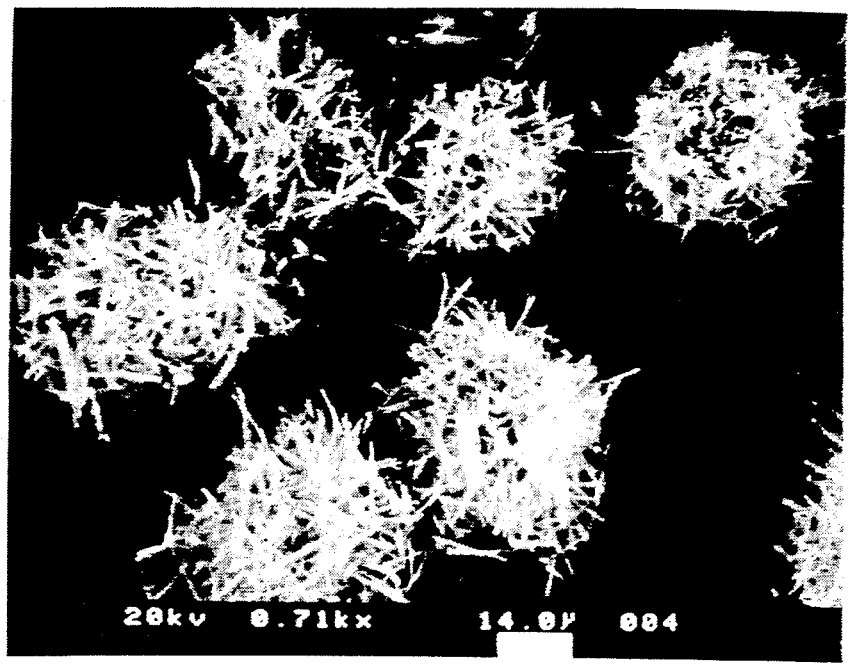
FIG. 14 is a micrograph showing the product resulting from gibbsite and pimelic acid.

This example was prepared and analyzed as in Example 5 except pimelic acid was used. FIG. 13 shows that XRD pattern of the new compound obtained compared to the starting materials. Chemical analysis shows that 0.277 moles of pimelic acid had reacted with one mole of gibbsite. The SEM is shown in FIG. 14.

EXAMPLE 7

Figure 16:
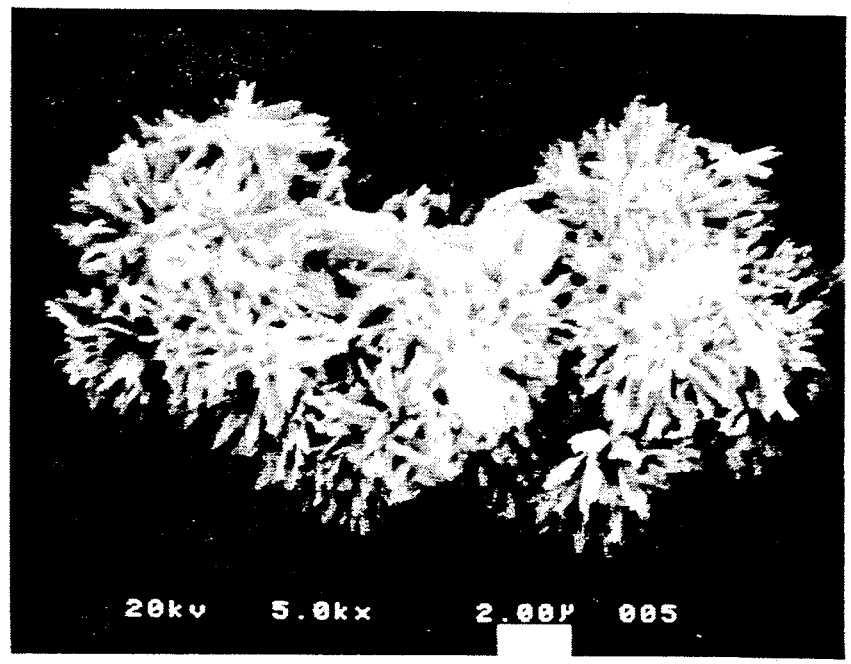
FIG. 16 is a micrograph showing the product resulting from gibbsite and itaconic acid.

This example was prepared and analyzed as in Example 6 except that 45 grams itaconic acid were used. FIG. 15 shows the XRD of the new compound compared to the starting materials and chemical analysis shows that 0.475 moles of itaconic acid had reacted with one mole of gibbsite. The SEM picture is shown in FIG. 16.

EXAMPLE 8

Figure 18:
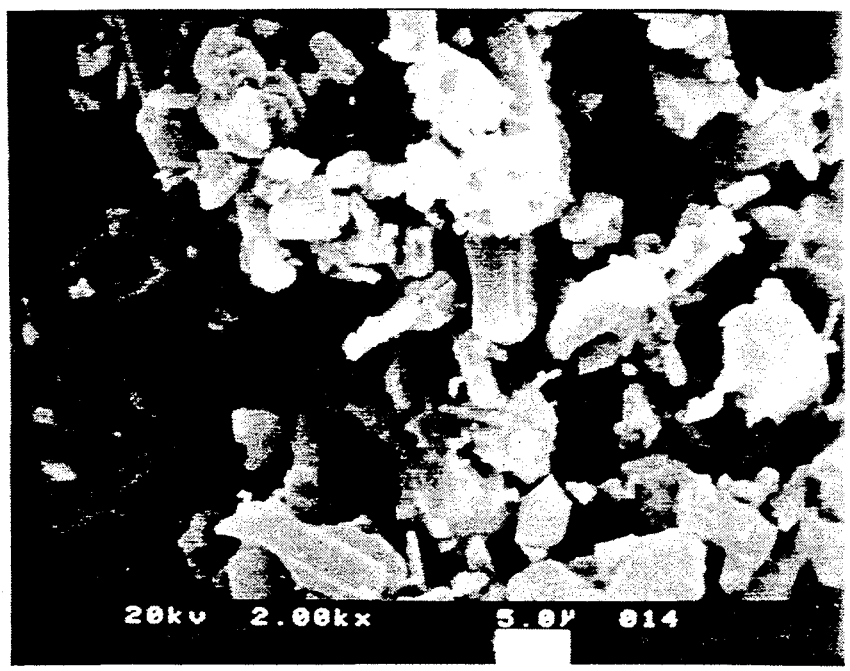
FIG. 18 is a micrograph showing the product resulting from boehmite and maleic acid.

In this example, the boehmite form of aluminum oxide-hydroxide was reacted with maleic acid. Amounts of reactants used were 25 g CATAPAL TM boehmite, 50 g maleic acid and 400 mls water, and the reaction was carried out at 185° C. FIG. 17 shows the XRD of this new compound, and the SEM picture is shown in FIG. 18.

Having thus described the invention, what is claimed is:

1. A method of preparing a water insoluble crystalline alumino-organic compounds having new characteristic x-ray diffraction patterns which do not correspond to the acid or anhydrous aluminum salt of the acid used and which have a chemical composition expressed in terms of molar ratios, by the formula:

$$M.n[R(COOH)_x]$$

wherein M is aluminum hydroxide, n is the number of moles of organic material reacted with a mole of M, R is an organic functional group and x is equal to or greater than 2, the method comprising reacting a mixture of an aluminum hydroxide material and an organic material in an aqueous solvent, the organic material containing at least two carboxylic acid groups to form said crystalline alumino-organic compound.

2. The method in accordance with claim 1 wherein M is $Al(OH)_3$.

3. The method in accordance with claim 1 wherein M is $AlO(OH)$.

4. The method in accordance with claim 1 wherein $R(COOH)_x$ is a dicarboxylic acid.

5. The method in accordance with claim 1 wherein $R(COOH)_x$ is selected from oxalic, malonic, maleic, succinic, glutaric, adipic, fumaric, tartaric, citric, pimelic and itaconic acids.

6. The method in accordance with claim 1 wherein n is in the range of 0.05 to 3.0 moles per mole of aluminum hydroxide.

7. The method in accordance with claim 1 wherein said aluminum hydroxide is gibbsite.

8. The method in accordance with claim 1 wherein said aluminum hydroxide is bayerite.

9. The method in accordance with claim 1 wherein said aluminum hydroxide is nordstrandite.

10. The method in accordance with claim 1 wherein said aluminum hydroxide is boehmite.

11. The method in accordance with claim 1 wherein prior to reacting, said organic material is dissolved in a liquid carrier.

12. The method in accordance with claim 11 wherein after dissolving, the organic material is mixed with the aluminum hydroxide.

13. The method in accordance with claim 1 wherein the mixture is heated for said reaction.

14. The method in accordance with claim 1 wherein the mixture is heated at a temperature of at least 100° C. for a time of at least 20 minutes.

15. The method in accordance with claim 1 wherein after said reacting, the compound is filtered, washed and dried.

16. A method of preparing a water insoluble crystalline alumino-organic compounds having new characteristic x-ray diffraction patterns which do not correspond to the acid or anhydrous aluminum salt of the acid used and which have a chemical composition expressed in terms of molar ratios, by the formula:

$$M.n[R(COOH)_x]$$

wherein M is aluminum hydroxide, n is the number of moles of organic material reacted with a mole of M, R is an organic functional group and x is equal to or greater than 2, the method comprising the steps of:

(a) dissolving an organic polycarboxylic acid in an aqueous base liquid solvent to provide a solution;
(b) adding aluminum hydroxide to said solution to form a mixture;
(c) heating said mixture to a temperature sufficient to cause said polycarboxylic acid to react with said aluminum hydroxide to form the alumino-organic compound; and
(d) recovering said alumino-organic compound.

17. The method in accordance with claim 16 wherein the polycarboxylic acid is selected from oxalic, malonic, maleic, succinic, glutaric, adipic, fumaric, tartaric, citric, pimelic and itaconic acids.

18. The method in accordance with claim 16 wherein the solvent is selected from water and alcohol.

19. The method in accordance with claim 16 wherein the aluminum hydroxide is $Al(OH)_3$.

20. The method in accordance with claim 16 wherein the aluminum hydroxide is $AlO(OH)$.

21. The method in accordance with claim 16 wherein the reaction is carried out between 100° and 300° C.

22. A method of preparing a water insoluble crystalline alumino-organic compounds having new characteristic x-ray diffraction patterns which do not correspond to the acid or anhydrous aluminum salt of the acid used and which have a chemical composition expressed in terms of molar ratios, by the formula:

$$M.n[R(COOH)_x]$$

wherein M is aluminum hydroxide, n is the number of moles of organic material reacted with a mole of M, R is an organic functional group and x is equal to or greater than 2, the method comprising the steps of:

(a) dissolving a polycarboxylic acid in water to provide a solution having an acid concentration in the range of 0.01 to 3.0 moles;
(b) adding aluminum hydroxide to said solution to provide a concentration thereof in the range of 0.1 to 3.0 moles per mole of polycarboxylic acid;
(c) heating said mixture to a temperature in the range of 100° to 250° C. to cause said acid to react with said aluminum hydroxide to form said crystalline alumino-organic compound; and
(d) recovering the compound from the solution.

23. The method in accordance with claim 16 wherein $R(COOH)_x$ is oxalic acid and the compound has an X-ray diffraction pattern designated B in FIG. 1.

24. The method in accordance with claim 16 wherein $R(COOH)_x$ is malonic acid.

25. The method in accordance with claim 16 wherein $R(COOH)_x$ is maleic acid and the compound has an X-ray diffraction pattern designated B in FIG. 5.

26. The method in accordance with claim 16 wherein $R(COOH)_x$ is succinic acid and the compound has an X-ray diffraction pattern designated B in FIG. 7.

27. The method in accordance with claim 16 wherein $R(COOH)_x$ is glutaric acid and the compound has an X-ray diffraction pattern designated B in FIG. 9.

28. The method in accordance with claim 16 wherein $R(COOH)_x$ is adipic acid.

29. The method in accordance with claim 16 wherein $R(COOH)_x$ is fumaric acid.

30. The method in accordance with claim 16 wherein $R(COOH)_x$ is tartaric acid.

31. The method in accordance with claim 16 wherein $R(COOH)_x$ is citric acid and the compound has an X-ray diffraction pattern designated B in FIG. 11.

32. The method in accordance with claim 16 wherein $R(COOH)_x$ is pimelic acid and the compound has an X-ray diffraction pattern designated B in FIG. 13.

33. The method in accordance with claim 16 wherein $R(COOH)_x$ is itaconic acid and the compound has an X-ray diffraction pattern designated B in FIG. 15.

34. A method of preparing a water insoluble crystalline alumino-organic compounds having new characteristic x-ray diffraction patterns which do not correspond to the acid or anhydrous aluminum salt of the acid used and which have a chemical composition expressed in terms of molar ratios, by the formula:

$$M.n[COOH]x$$

wherein M is aluminum hydroxide, n is the number of moles of organic material reacted with a mole of M and x is equal to or greater than 2, the method comprising reacting a mixture of an aluminum hydroxide material and oxalic acid to form said crystalline alumino-organic compound, the compound having an X-ray diffraction pattern designated B in FIG. 1.

35. The method in accordance with claim 22 wherein the aluminum hydroxide is gibbsite.

36. The method in accordance with claim 22 wherein the aluminum hydroxide is bayerite.

37. The method in accordance with claim 22 wherein the aluminum hydroxide is boehmite.

38. The method in accordance with claim 22 wherein the aluminum hydroxide is nordstrandite.

39. The method in accordance with claim 22 wherein the aluminum hydroxide is a gel.

40. The method in accordance with claim 22 wherein M is magnesium hydroxide.

41. The method in accordance with claim 22 wherein M is gallium hydroxide.

42. The method in accordance with claim 22 wherein M is zinc hydroxide.

43. The method in accordance with claim 22 wherein $R(COOH)_x$ is oxalic acid and the compound has an X-ray diffraction pattern designated B in FIG. 1.

44. The method in accordance with claim 22 wherein $R(COOH)_x$ is malonic acid.

45. The method in accordance with claim 22 wherein $R(COOH)_x$ is maleic acid and the compound has an X-ray diffraction pattern designated B in FIG. 5.

46. The method in accordance with claim 22 wherein $R(COOH)_x$ is succinic acid and the compound has an X-ray diffraction pattern designated B in FIG. 7.

47. The method in accordance with claim 22 wherein $R(COOH)_x$ is glutaric acid and the compound has an X-ray diffraction pattern designated B in FIG. 9.

48. The method in accordance with claim 22 wherein $R(COOH)_x$ is adipic acid.

49. The method in accordance with claim 22 wherein $R(COOH)_x$ is furmaric acid.

50. The method in accordance with claim 22 wherein $R(COOH)_x$ is tartaric acid.

51. The method in accordance with claim 22 wherein $R(COOH)_x$ is citric acid and the compound has an X-ray diffraction pattern designated B in FIG. 11.

52. The method in accordance with claim 22 wherein $R(COOH)_x$ is pimelic acid and the compound has an X-ray diffraction pattern designated B in FIG. 13.

53. The method in accordance with claim 22 wherein $R(COOH)_x$ is itaconic acid and the compound has an X-ray diffraction pattern designated B in FIG. 15.

54. A water insoluble crystalline anhydrous compound having new characteristic x-ray diffraction patterns which do not correspond to the acid or anhydrous aluminum salt of the acid used and which have a chemical composition expressed in terms of molar ratios, by the formula:

$$M.n[R(COOH)_x]$$

wherein M is a metal hydroxide selected from aluminum hydroxide, n is the number of moles of organic material reacted with a mole of M, R is an organic functional group and x is equal to or greater than 2.

55. The compound in accordance with claim 54 wherein $R(COOH)_x$ is oxalic acid and the compound has an X-ray diffraction pattern designated B in FIG. 1.

56. The compound in accordance with claim 54 wherein $R(COOH)_x$ is malonic acid.

57. The compound in accordance with claim 54 wherein $R(COOH)_x$ is maleic acid and the compound has an X-ray diffraction pattern designated B in FIG. 5.

58. The compound in accordance with claim 54 wherein $R(COOH)_x$ is succinic acid and the compound has an X-ray diffraction pattern designated B in FIG. 7.

59. The compound in accordance with claim 54 wherein $R(COOH)_x$ is glutaric acid and the compound has an X-ray diffraction pattern designated B in FIG. 9.

60. The compound in accordance with claim 54 wherein $R(COOH)_x$ is adipic acid.

61. The compound in accordance with claim 54 wherein $R(COOH)_x$ is furmaric acid.

62. The compound in accordance with claim 54 wherein $R(COOH)_x$ is tartaric acid.

63. The compound in accordance with claim 54 wherein $R(COOH)_x$ is citric acid and the compound has an X-ray diffraction pattern designated B in FIG. 11.

64. The compound in accordance with claim 54 wherein $R(COOH)_x$ is pimelic acid and the compound has an X ray diffraction pattern designated B in FIG. 13.

65. The compound in accordance with claim 54 wherein $R(COOH)_x$ is itaconic acid and the compound has an X-ray diffraction pattern designated B in FIG. 15.

66. A water insoluble crystalline anhydrous compound having new characteristic x-ray diffraction patterns which do not correspond to the acid or anhydrous aluminum salt of the acid used and which have a chemical composition expressed in terms of molar ratios, by the formula:

$$M.n[COOH]x$$

wherein M is aluminum hydroxide, n is the number of moles of organic material reacted with a mole of M and x is equal to or greater than 2 and the compound has an X-ray diffraction pattern designated B in FIG. 1.

67. The compound in accordance with claim 54 wherein the aluminum hydroxide is gibbsite.

68. The compound in accordance with claim 54 wherein the aluminum hydroxide is bayerite.

69. The compound in accordance with claim 54 wherein the aluminum hydroxide is boehmite.

70. The compound in accordance with claim 54 wherein the aluminum hydroxide is nordstrandite.

71. The compound in accordance with claim 54 wherein the aluminum hydroxide is a gel.

72. The compound in accordance with claim 54 wherein M is magnesium hydroxide.

73. The compound in accordance with claim 54 wherein M is gallium hydroxide.

74. The compound in accordance with claim 54 wherein M is zinc hydroxide.

75. A water insoluble crystalline anhydrous compound having new characteristic x-ray diffraction patterns which do not correspond to the acid or anhydrous aluminum salt of the acid used and which have a chemical composition expressed in terms of molar ratios, by the formula:

$$M \cdot n[R(COOH)_x]$$

wherein M is aluminum hydroxide, n is in the range of 0.01 to 3.0 and is the number of moles of organic material reacted with a mole of M, R is an organic functional group having 0 to 15 carbon atoms and x is in the range of 2 to 4.

76. The compound in accordance with claim 75 wherein $R(COOH)_x$ is oxalic acid and the compound has an X-ray diffraction pattern designated B in FIG. 1.

77. The compound in accordance with claim 75 wherein $R(COOH)_x$ is malonic acid.

78. The compound in accordance with claim 75 wherein $R(COOH)_x$ is maleic acid and the compound has an X-ray diffraction pattern designated B in FIG. 5.

79. The compound in accordance with claim 75 wherein $R(COOH)_x$ is succinic acid and the compound has an X-ray diffraction pattern designated B in FIG. 7.

80. The compound in accordance with claim 75 wherein $R(COOH)_x$ is glutaric acid and the compound has an X-ray diffraction pattern designated B in FIG. 9.

81. The compound in accordance with claim 75 wherein $R(COOH)_x$ is adipic acid.

82. The compound in accordance with claim 75 wherein $R(COOH)_x$ is furmaric acid.

83. The compound in accordance with claim 75 wherein $R(COOH)_x$ is tartaric acid.

84. The compound in accordance with claim 75 wherein $R(COOH)_x$ is citric acid and the compound has an X-ray diffraction pattern designated B in FIG. 11.

85. The compound in accordance with claim 75 wherein $R(COOH)_x$ is pimelic acid and the compound has an X-ray diffraction pattern designated B in FIG. 13.

86. The compound in accordance with claim 75 wherein $R(COOH)_x$ is itaconic acid and the compound has an X-ray diffraction pattern designated B in FIG. 15.

87. The compound in accordance with claim 54 wherein n is in the range of from 0.05 to 3.0 moles.

88. The compound in accordance with claim 54 wherein M is $Al(OH)_3$.

89. The compound in accordance with claim 54 wherein R is a monomer, oligomer or short chain polymer.

90. The compound in accordance with claim 66 wherein n is in the range of 0.05 to 1.

91. A water insoluble crystalline anhydrous compound having new characteristic x-ray diffraction patterns which do not correspond to the acid or anhydrous aluminum salt of the acid used and which have a chemical composition expressed in terms of molar ratios, by the formula:

$$Al_2O_3 \cdot 3H_2O \ [R \ (COOH)_{x=2}]_{n=.05 \ to \ 2}$$

wherein R is an organic group, x is the number of dicarboxylic acid groups and n is the number of moles of organic material reacted with a mole of aluminum hydroxide.

92. A water insoluble crystalline anhydrous compound having new characteristic x-ray diffraction patterns which do not correspond to the acid or anhydrous aluminum salt of the acid used, the compound comprised of aluminum hydroxide and polycarboxylic acid, the polycarboxylic acid being present in the compound on a mole basis in the range of 0.05 to 2 moles per mole of aluminum hydroxide.

93. A water insoluble crystalline anhydrous compound having new characteristic x-ray diffraction patterns which do not correspond to the acid or anhydrous aluminum salt of the acid used, the compound comprised of oxalic acid and gibbsite, the acid being present in the compound on a mole basis in the range of 0.05 to 1 moles per mole of said material, the compound having an X-ray diffraction pattern designated B in FIG. 1.

94. A water insoluble crystalline anhydrous compound having new characteristic x-ray diffraction patterns which do not correspond to the acid or anhydrous aluminum salt of the acid used, the compound comprised of malonic acid and gibbsite, the acid being present in the compound on a mole basis in the range of 0.01 to 3 moles per mole of said material, the compound having an X-ray diffraction pattern designated B in FIG. 2.

95. A water insoluble crystalline anhydrous compound having new characteristic x-ray diffraction patterns which do not correspond to the acid or anhydrous aluminum salt of the acid used, the compound comprised of maleic acid and boehmite, the acid being present in the compound on a mole basis in the range of 0.01 to 3 moles per mole of said material, the compound having an X-ray diffraction pattern designated B in FIG. 17.

96. A water insoluble crystalline anhydrous compound having new characteristic x-ray diffraction patterns which do not correspond to the acid or anhydrous aluminum salt of the acid used, the compound comprised of succinic acid and gibbsite, the acid being present in the compound on a mole basis in the range of 0.01 to 3 moles per mole of said material, the compound having an X-ray diffraction pattern designated B in FIG. 7.

97. A water insoluble crystalline anhydrous compound having new characteristic x-ray diffraction patterns which do not correspond to the acid or anhydrous aluminum salt of the acid used, the compound comprised of glutaric acid and gibbsite, the acid being present in the compound on a mole basis in the range of 0.01 to 3 moles per mole of said material, the compound having an X-ray diffraction pattern designated B in FIG. 9.

98. A water insoluble crystalline anhydrous compound having new characteristic x-ray diffraction patterns which do not correspond to the acid or anhydrous aluminum salt of the acid used, the compound comprised of adipic acid and gibbsite, the acid being present in the compound on a mole basis in the range of 0.01 to 3 moles per mole of said material.

99. A water insoluble crystalline anhydrous compound having new characteristic x-ray diffraction patterns which do not correspond to the acid or anhydrous aluminum salt of the acid used, the compound comprised of fumaric acid and gibbsite, the acid being present in the compound on a mole basis in the range of 0.01 to 3 moles per mole of said material.

100. A water insoluble crystalline anhydrous compound having new characteristic x-ray diffraction patterns which do not correspond to the acid or anhydrous aluminum salt of the acid used, the compound comprised of citric acid and gibbsite, the acid being present in the compound on a mole basis in the range of 0.01 to 3 moles per mole of said material, the compound having an X-ray diffraction pattern designated B in FIG. 11.

101. A water insoluble crystalline anhydrous compound having new characteristic x-ray diffraction patterns which do not correspond to the acid or anhydrous aluminum salt of the acid used, the compound comprised of itaconic acid and gibbsite, the acid being present in the compound on a mole basis in the range of 0.01 to 3 moles per mole of said material, the compound having an X-ray diffraction pattern designated B in FIG. 15.

102. A water insoluble crystalline anhydrous compound having new characteristic x-ray diffraction patterns which do not correspond to the acid or anhydrous aluminum salt of the acid used, the compound comprised of pimelic acid and gibbsite, the acid being present in the compound on a mole basis in the range of 0.01 to 3 moles per mole of said material, the compound having an X-ray diffraction pattern designated B in FIG. 13.

103. The product in accordance with claim 91 wherein R(COOH) is oxalic acid and the compound has an X-ray diffraction pattern designated B in FIG. 1.

104. The product in accordance with claim 91 wherein R(COOH) is malonic acid.

105. The product in accordance with claim 91 wherein R(COOH) is maleic acid and the compound has an X-ray diffraction pattern designated B in FIG. 5.

106. The product in accordance with claim 91 wherein R(COOH) is succinic acid and the compound has an X-ray diffraction pattern designated B in FIG. 7.

107. The product in accordance with claim 91 wherein R(COOH) is glutaric acid and the compound has an X-ray diffraction pattern designated B in FIG. 9.

108. The product in accordance with claim 91 wherein R(COOH) is adipic acid.

109. The product in accordance with claim 91 wherein R(COOH) is fumaric acid.

110. The product in accordance with claim 91 wherein R(COOH) is itaconic acid and the compound has an X-ray diffraction pattern designated B in FIG. 15.

* * * * *